United States Patent
Armbruster

(10) Patent No.: US 10,045,866 B2
(45) Date of Patent: Aug. 14, 2018

(54) PROSTHETIC ATTACHMENT

(71) Applicant: Michael Armbruster, San Diego, CA (US)

(72) Inventor: Michael Armbruster, San Diego, CA (US)

( * ) Notice: Subject to any disclaimer, the term of this patent is extended or adjusted under 35 U.S.C. 154(b) by 0 days.

(21) Appl. No.: 15/088,820

(22) Filed: Apr. 1, 2016

(65) Prior Publication Data

US 2017/0281369 A1   Oct. 5, 2017

(51) Int. Cl.
| | |
|---|---|
| *A61F 2/54* | (2006.01) |
| *A61F 2/56* | (2006.01) |
| *A61F 2/76* | (2006.01) |
| *A61F 2/58* | (2006.01) |
| *A61B 50/20* | (2016.01) |
| *A61F 2/50* | (2006.01) |
| *B25J 15/06* | (2006.01) |
| *B25J 15/04* | (2006.01) |

(52) U.S. Cl.
CPC ............ *A61F 2/588* (2013.01); *A61F 2/76* (2013.01); *A44D 2203/00* (2013.01); *A61B 2050/21* (2016.02); *A61F 2002/5018* (2013.01); *A61F 2002/5083* (2013.01); *A61F 2210/009* (2013.01); *A61F 2220/0041* (2013.01); *B25J 15/0441* (2013.01); *B25J 15/0608* (2013.01)

(58) Field of Classification Search
CPC .......... B25J 15/0441; A61B 2050/0079; A61B 2050/21
See application file for complete search history.

(56) References Cited

U.S. PATENT DOCUMENTS

| | | | | |
|---|---|---|---|---|
| 2005/0278903 | A1* | 12/2005 | Dunaye | A44C 5/2071 24/303 |
| 2007/0179493 | A1* | 8/2007 | Kim | A61B 17/7062 606/33 |
| 2012/0255144 | A1* | 10/2012 | Gaudillere | A44B 11/266 24/303 |
| 2017/0225339 | A1* | 8/2017 | Kerestes | B25J 15/0441 |

* cited by examiner

*Primary Examiner* — David H Willse
(74) *Attorney, Agent, or Firm* — John R. Ross; John R. Ross, III

(57) ABSTRACT

A prosthetic attachment for a prosthetic limb. A base is attached to the prosthetic limb. The base has a magnet that is surrounded by base valleys and base peaks. An attachment piece is attached to the prosthetic attachment. The attachment piece also has a magnet that is surrounded by attachment piece valleys and attachment piece peaks. The magnetic force between the base magnet and the attachment piece magnet attracts the prosthetic attachment to the prosthetic limb so that the base peaks and valleys mates with the attachment piece peaks and valleys for a secure removable attachment. In a preferred embodiment a locking device is used to further secure the prosthetic attachment to the prosthetic limb. In a preferred embodiment the prosthetic attachment is a prosthetic hand and the prosthetic limb is a prosthetic arm.

10 Claims, 11 Drawing Sheets

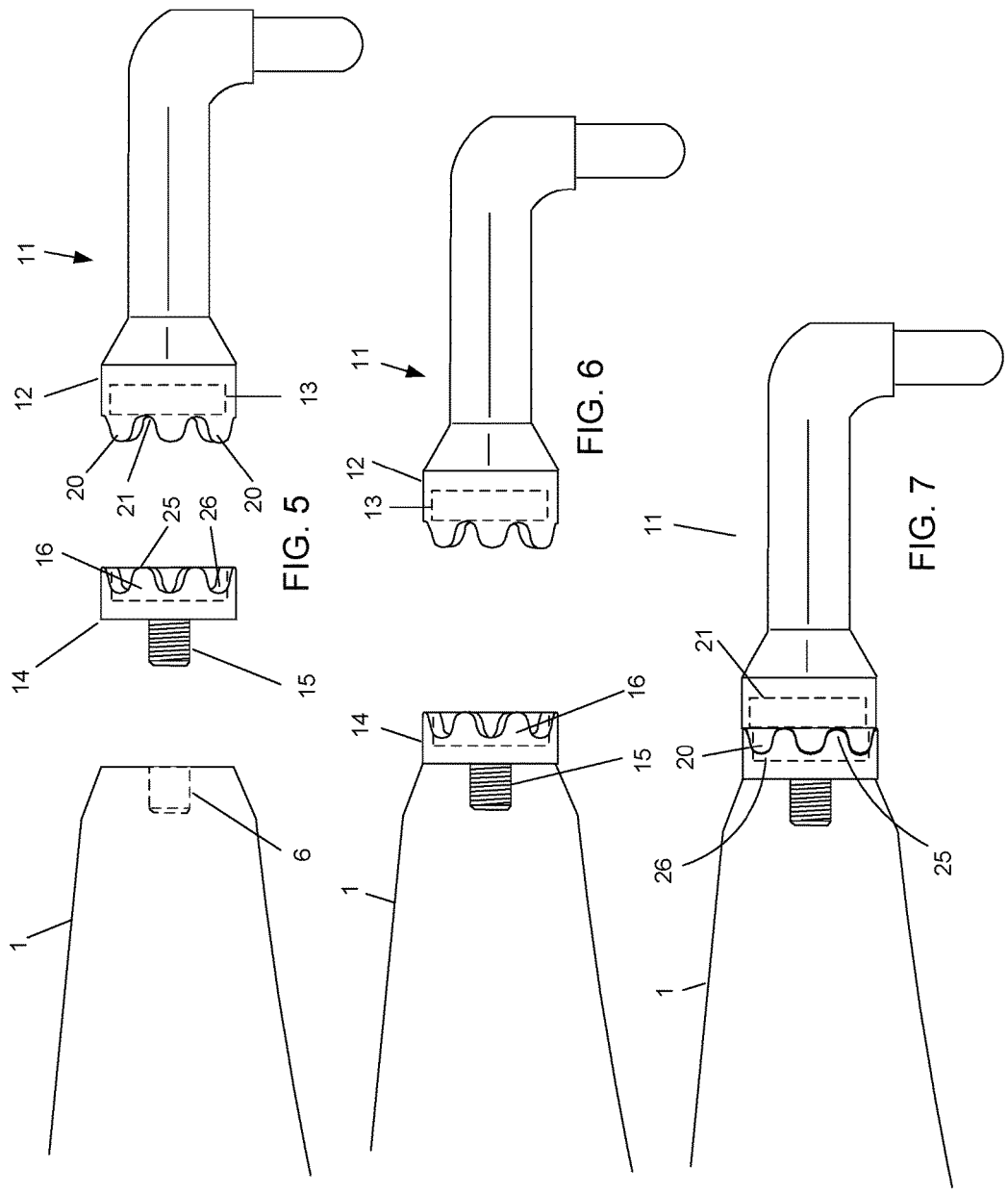

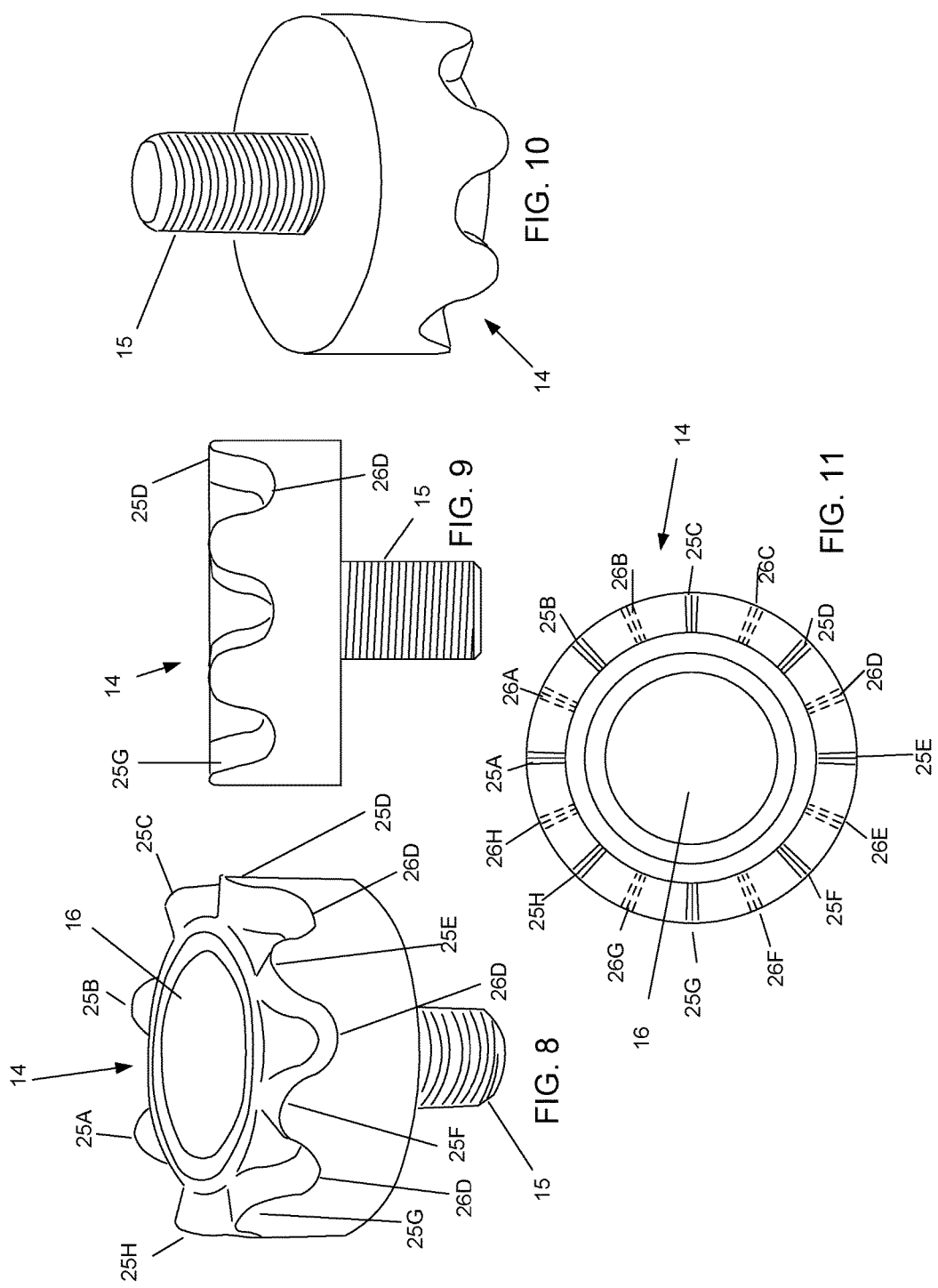

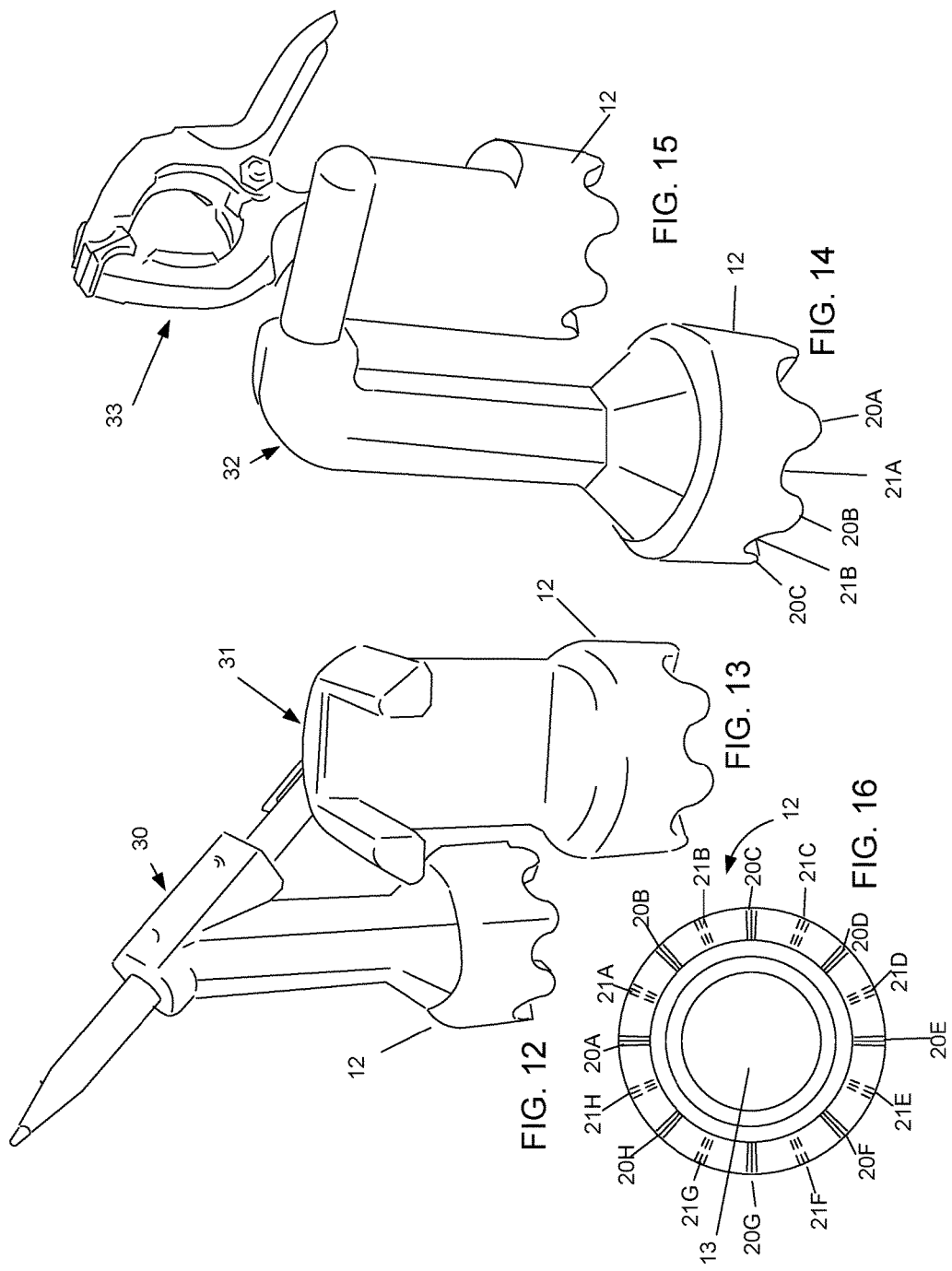

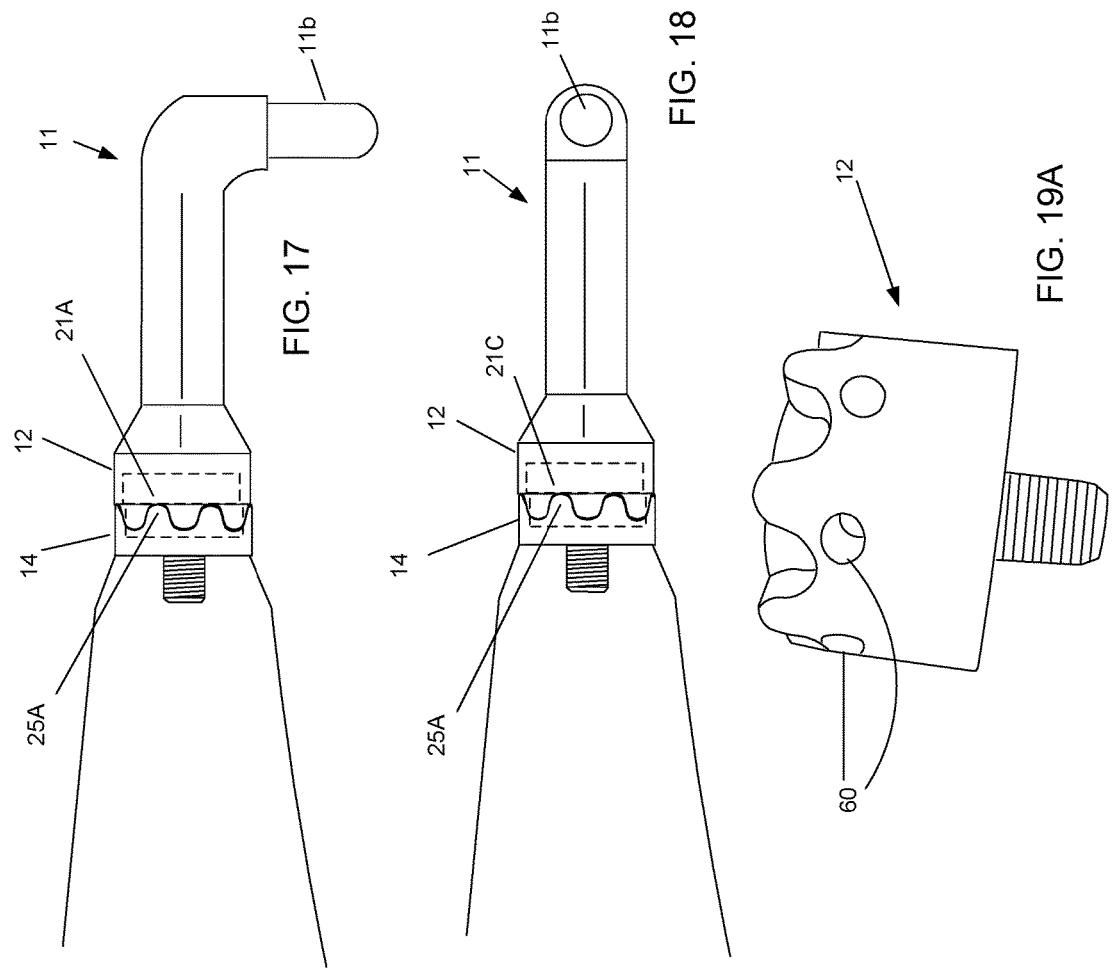

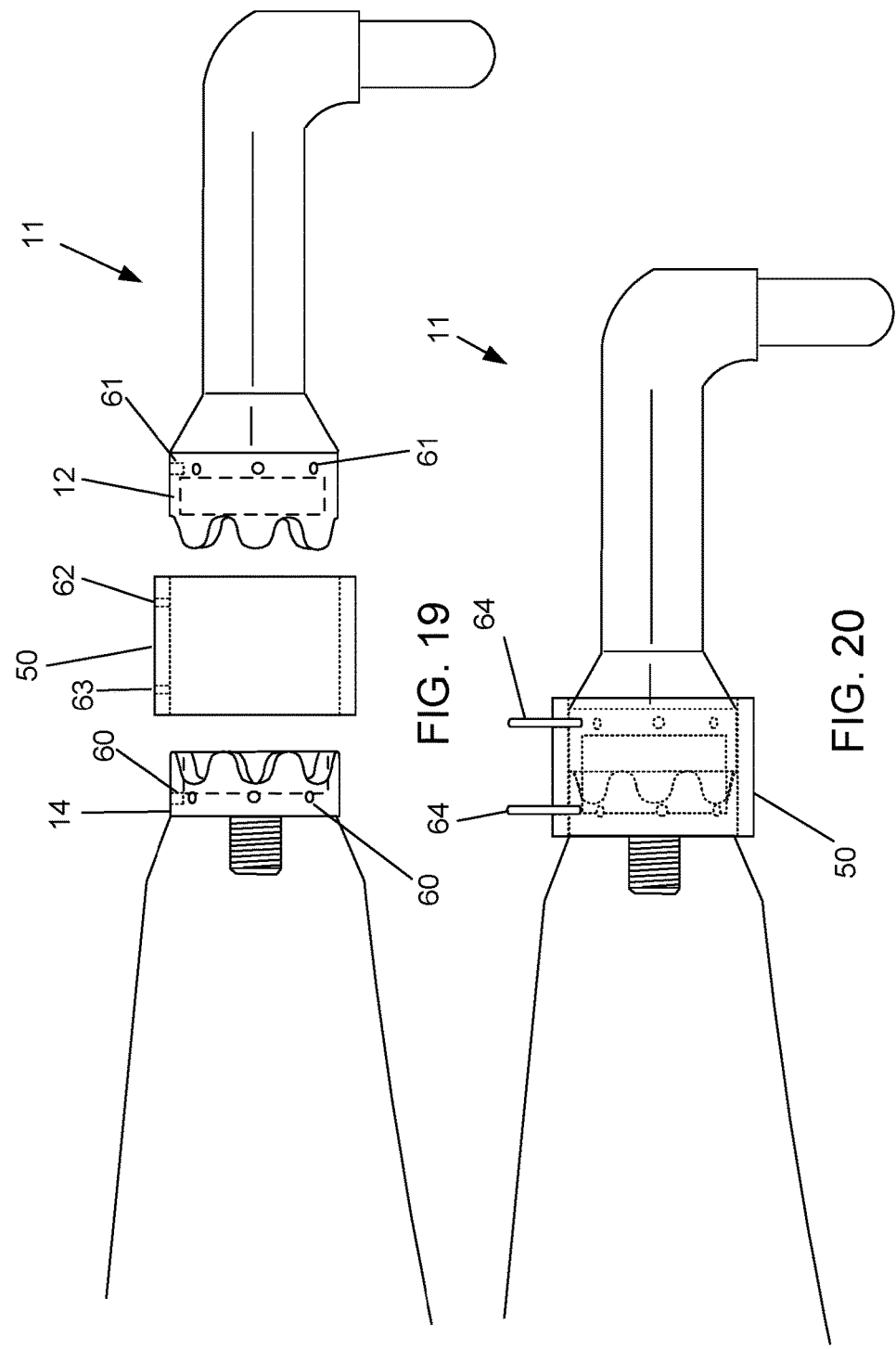

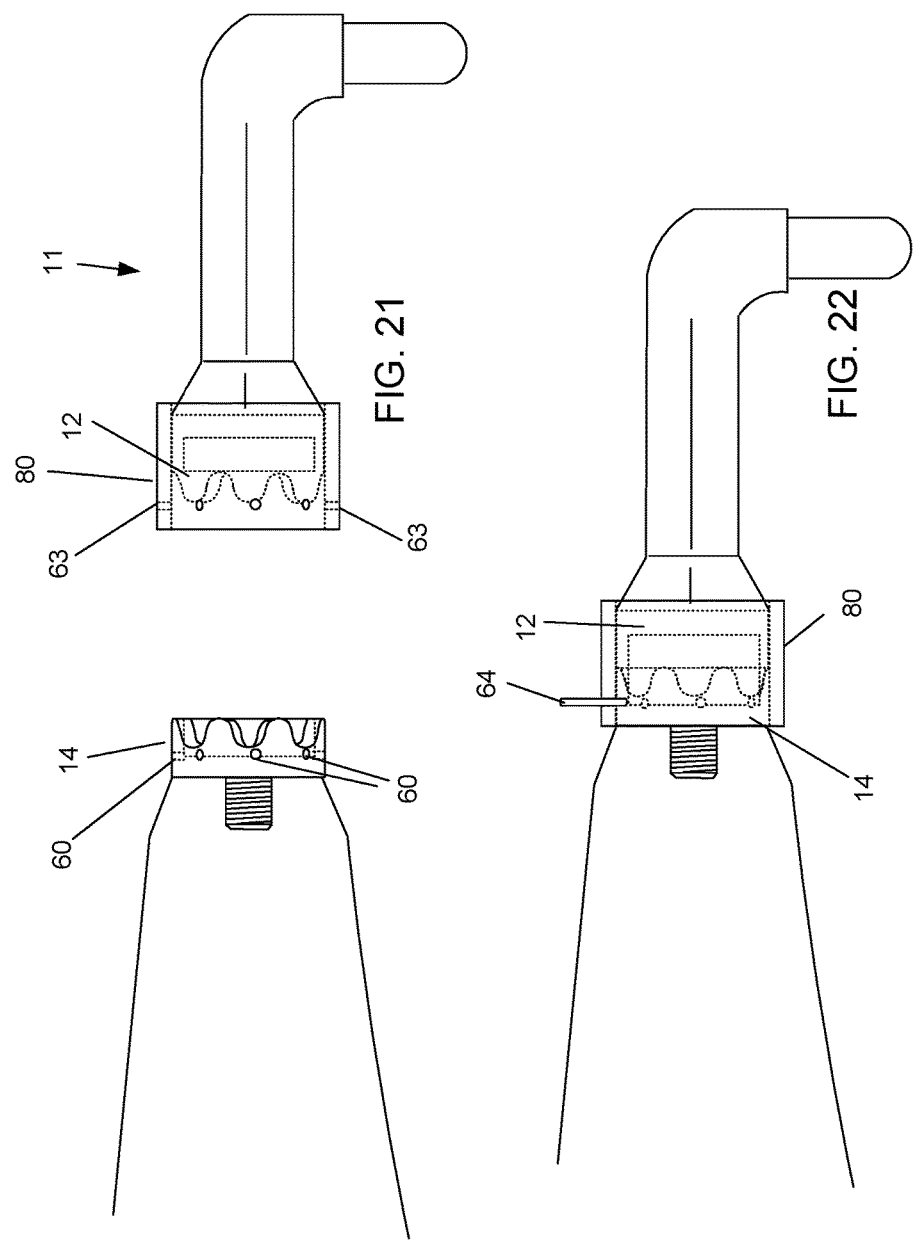

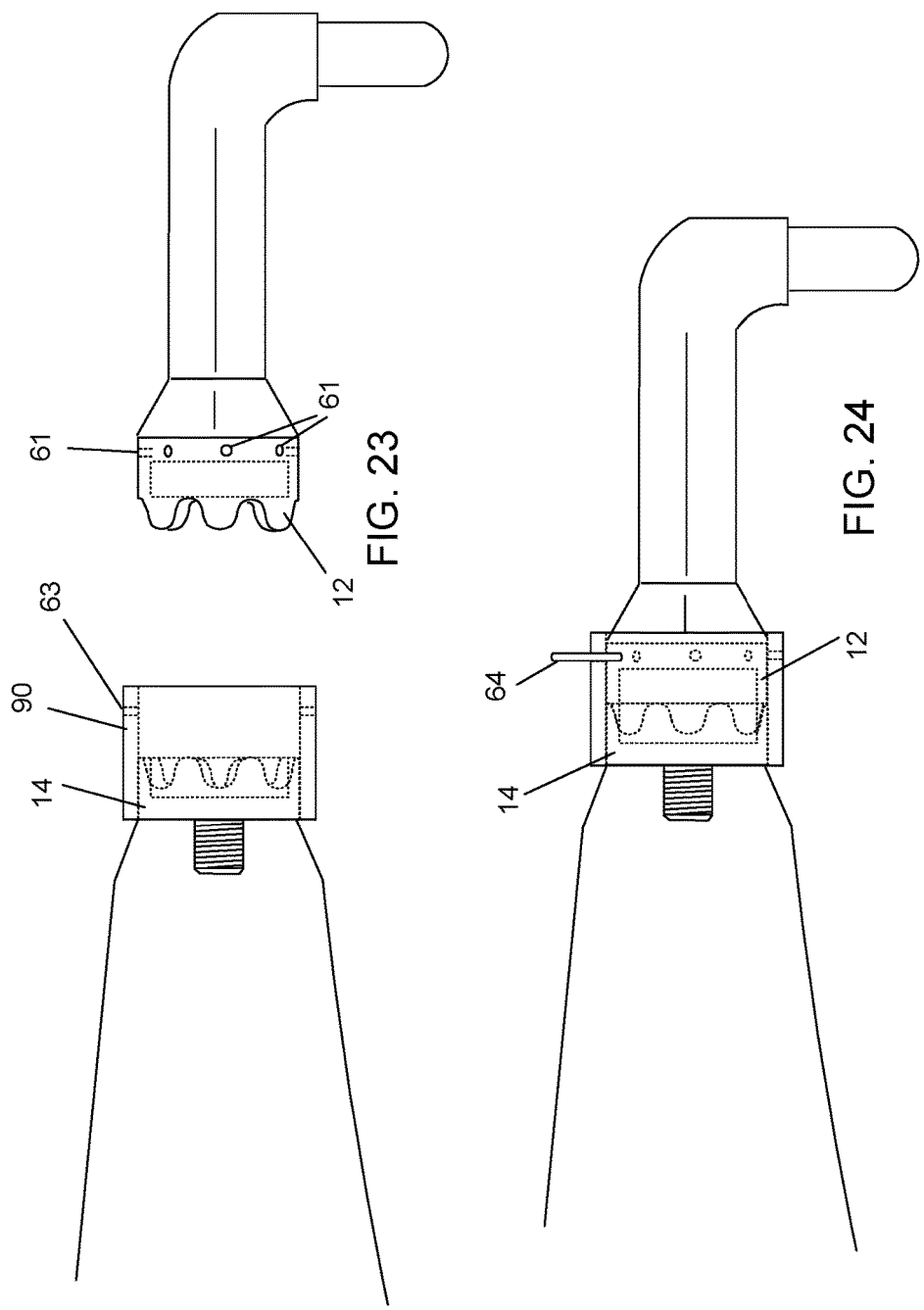

PROSTHETIC ATTACHMENT

The present invention relates to prosthetic limbs, and in particular, to prosthetic attachments to prosthetic limbs.

BACKGROUND OF THE INVENTION

Prosthetic arms are well known. A prosthetic arm is an artificially made substitute for an arm, or portion of an arm, that was perhaps lost through a congenital defect, accident, illness, or wartime injury.

Many prosthetic arms will not contain a permanent hand. Rather, the prosthetic arm will end at the wrist, wherein the user can then screw in the hand (hereinafter "prosthetic attachment"). FIG. 1 shows prosthetic attachment 4 removably attached to prosthetic arm 1. It is desirable to have attachments that are removable so that the user may change the style depending upon the current need. For example, the user may be in a social setting and might therefore want the attachment to resemble a traditional hand, even though the hand may have limited functionality. On another occasion the user may need to do a lot of heavy lifting, in which case the attachment may be a hook.

The prior art method of attaching hand 4 to arm 1 is via threaded bolt 5 (FIGS. 2-4). Bolt 5 is threaded into internal threads 6 of prosthetic arm 1. Utilizing the prior art method of attachment, the user must correctly thread hand 4 onto arm 1 and turn hand 1 until appropriately tightened and positioned at the correct angle. This can be time consuming and very challenging to individuals with multiple limb problems, children or the elderly.

What is needed is a better more efficient way of attaching a removably attached prosthetic attachment to a prosthetic limb.

SUMMARY OF THE INVENTION

The present invention provides a prosthetic attachment for a prosthetic limb. A base is attached to the prosthetic limb. The base has a magnet that is surrounded by base valleys and base peaks. An attachment piece is attached to the prosthetic attachment. The attachment piece also has a magnet that is surrounded by attachment piece valleys and attachment piece peaks. The magnetic force between the base magnet and the attachment piece magnet attracts the prosthetic attachment to the prosthetic limb so that the base peaks and valleys mates with the attachment piece peaks and valleys for a secure removable attachment. In a preferred embodiment a locking device is used to further secure the prosthetic attachment to the prosthetic limb. In a preferred embodiment the prosthetic attachment is a prosthetic hand and the prosthetic limb is a prosthetic arm.

BRIEF DESCRIPTION OF THE DRAWINGS

FIGS. 5-7 show a preferred embodiment of the present invention.

FIGS. 8-11 show a preferred base.

FIGS. 12-15 show preferred prosthetic attachments.

FIG. 16 shows a bottom view of a preferred attachment piece.

FIGS. 17-18 show alternative attachment angles.

FIG. 19A shows another preferred base with locking holes.

FIGS. 19-20 show another preferred embodiment of the present invention.

FIGS. 21-22 show another preferred embodiment of the present invention.

FIGS. 23-24 show another preferred embodiment of the present invention.

DETAILED DESCRIPTION OF THE PREFERRED EMBODIMENTS

Figure 1:
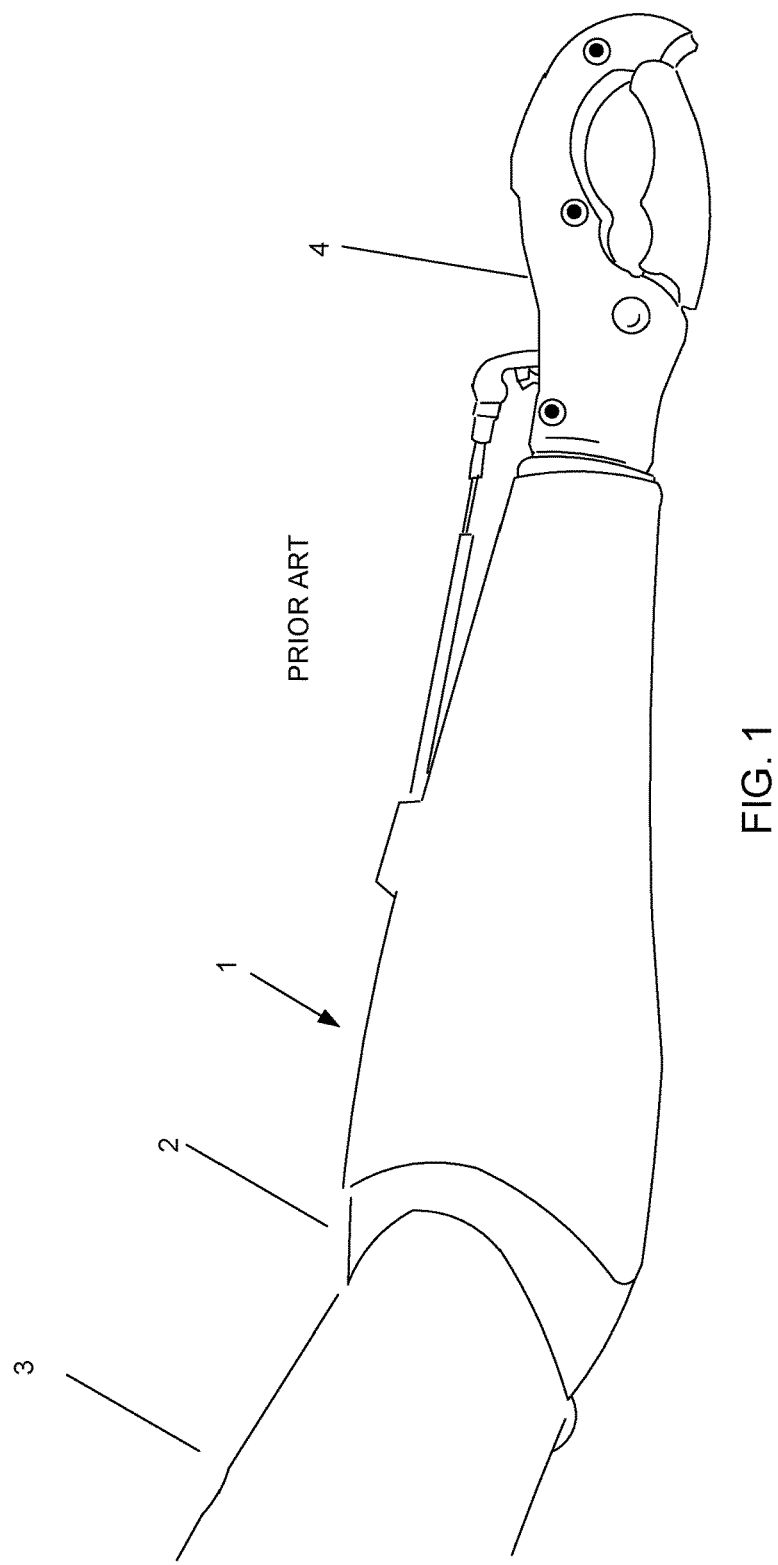
FIG. 1 shows a prior art prosthetic arm connected to a user's residual limb.
Figure 2:
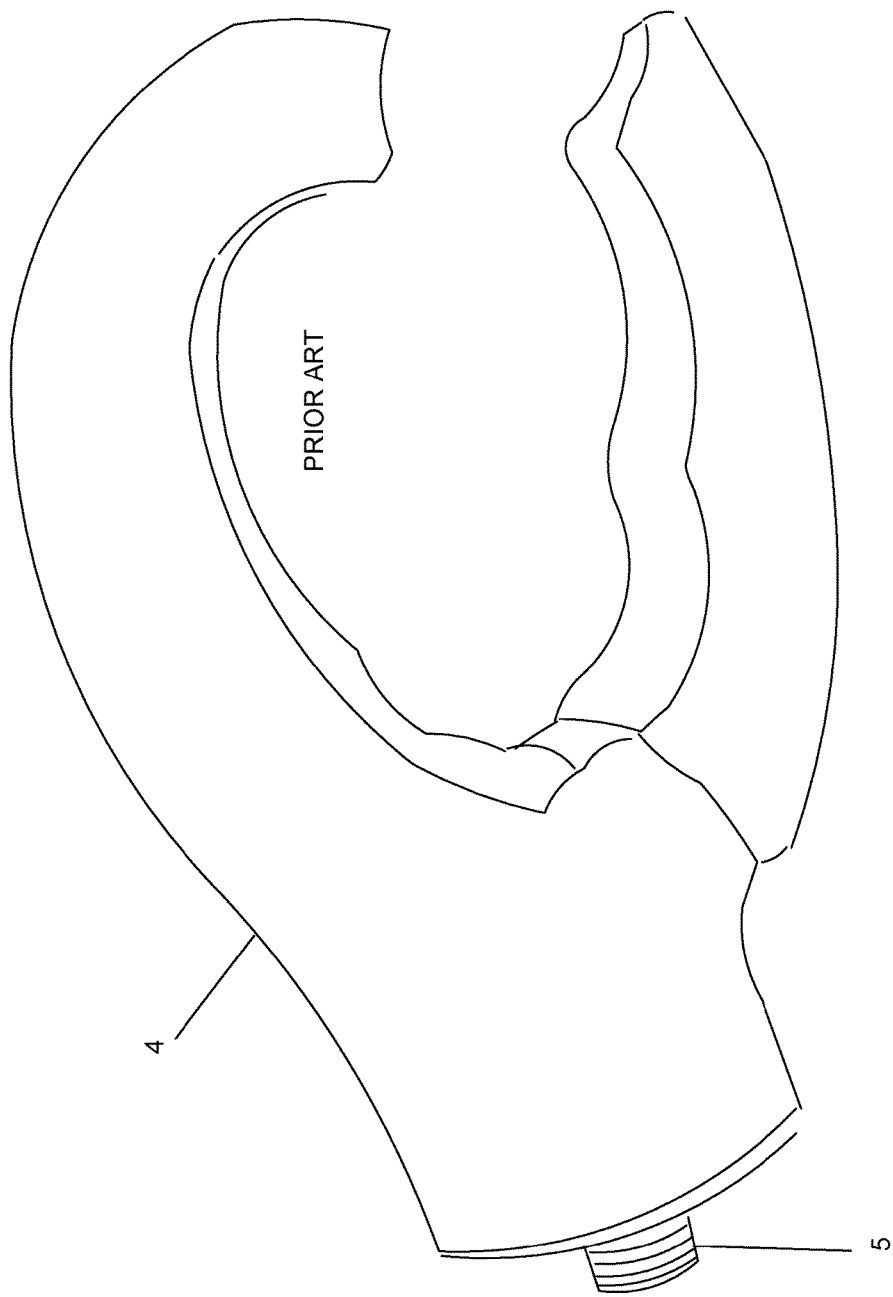
FIG. 2 shows a prior art prosthetic hand.
Figure 3:
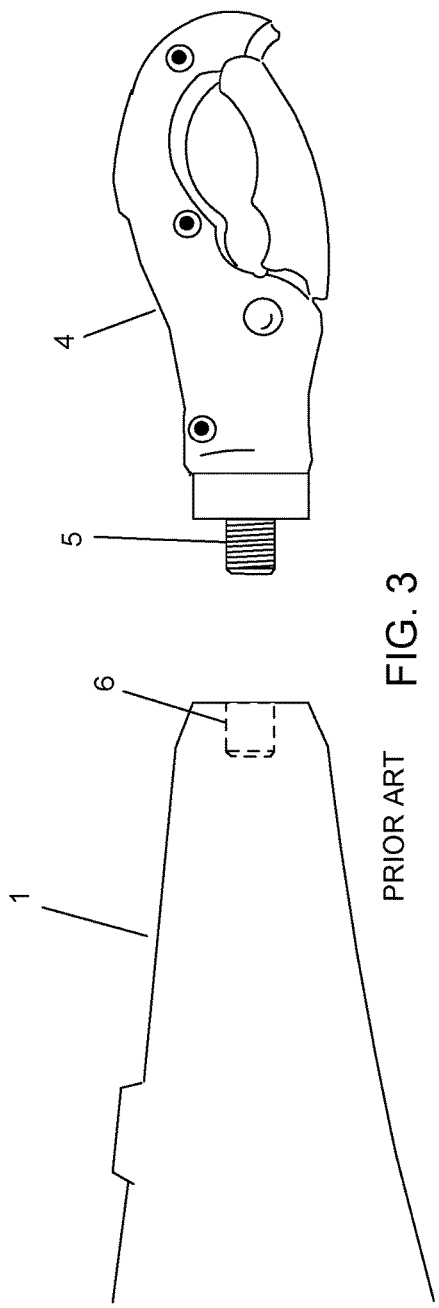
FIGS. 3-4 show a prior art removable connection to a prosthetic arm.
Figure 4:
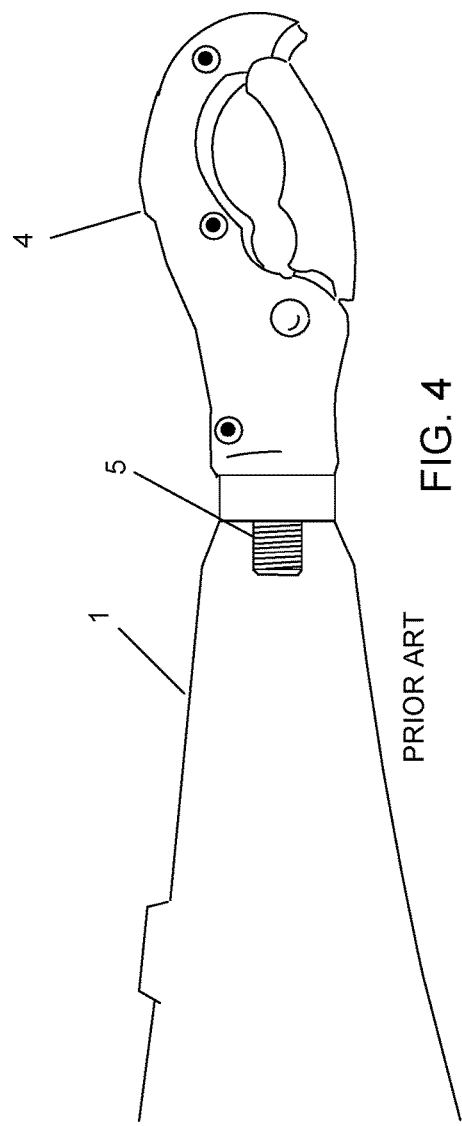
Figure 25:
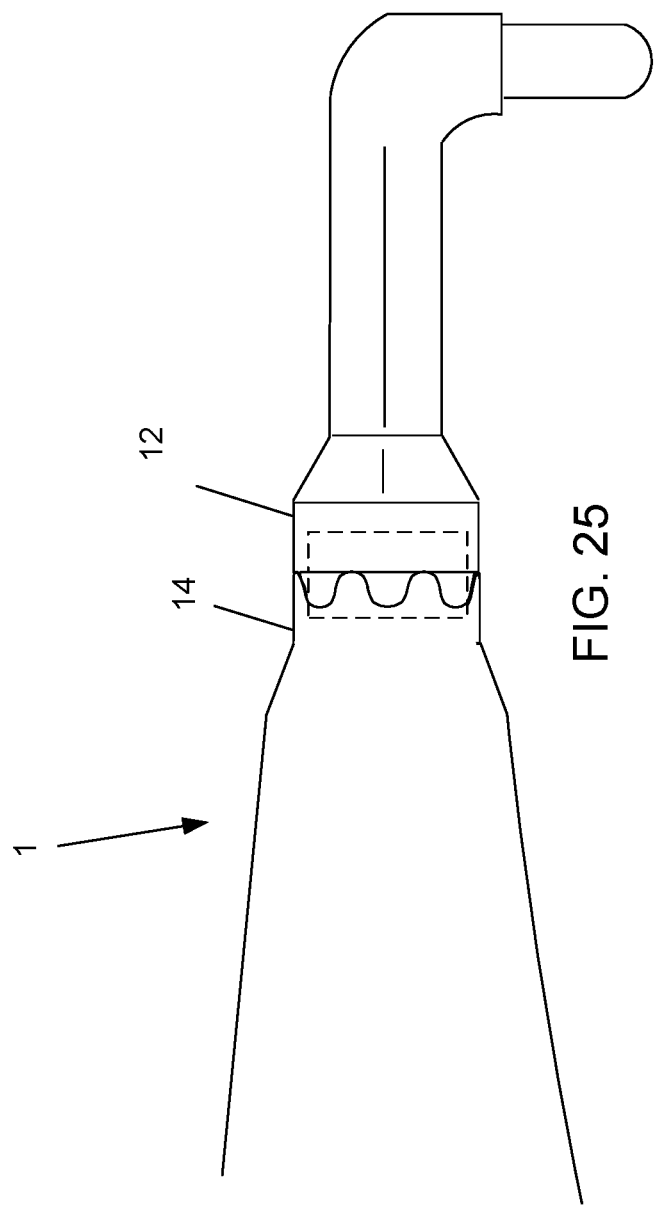
FIG. 25 shows another preferred embodiment of the present invention.

In the present invention, a base is screwed into the wrist of the user's [already existing] prosthetic arm. This base contains an embedded magnet. A prosthetic attachment includes a prosthetic attachment piece that also has an embedded magnet. The user can simply place the base near the attachment piece, the magnets will then attract to each other, and the prosthetic attachment will click into place. Removing the attachment is equally as easy given it can be pulled away without the need of a fully developed hand. The base has curved teeth, (hereinafter referred to as "valleys and peaks"), along the perimeter. This prevents unwanted clockwise and counter-clockwise movement, while still allowing the user to easily adjust the attachment to the appropriate angle. Finally, in a preferred embodiment the invention contains a basic locking mechanism for applications where the magnetic pull alone might not be strong enough to keep the attachment in place, such as lifting a heavy object.

FIGS. 5-7 show side views of a first preferred embodiment of the present invention. Removably attached prosthetic attachment 11 includes attachment piece 12. Attachment piece 12 includes embedded attachment magnet 13. Base 14 includes attachment bolt 15 and is threaded into internal threads 6 of prosthetic arm 1. Base 14 further includes base magnet 16. Attachment piece 12 includes a plurality of peaks 20 and valleys 21 that mate with peaks 25 and valleys 26 of base 14.

FIG. 6 shows base 14 rigidly attached to prosthetic arm 1 via bolt 15. Prosthetic attachment 11 is being moved closer to base 14. As prosthetic attachment 11 is moved closer the magnetic attractive force between magnets 13 and 16 becomes sufficient to pull prosthetic attachment 11 close to prosthetic arm 1 so that attachment piece 12 and base 14 are rigidly connected (FIG. 7). Valleys 21 and 26 and peaks 25 and 20 function to guide prosthetic attachment 11 so that it is appropriately mated with prosthetic arm 1 as shown in FIG. 7.

Base

FIGS. 8-11 show a preferred base 14. Magnet 16 is rigidly embedded into base 14 as shown, via a pressure fit. Bolt 15 is rigidly connected to base 14. Contoured valleys 26A-26H and contoured peaks 25A-25H surround base 14 at its perimeter. Base 14 is preferably plastic and preferably fabricated via an injection molded process.

Prosthetic Attachments

FIGS. 12-15 show prosthetic attachments 30-33. The user has the option of choosing whichever attachment he prefers. For example, prosthetic attachment 30 is useful for holding a writing implement, prosthetic attachment 31 is useful for picking up things, prosthetic attachment 32 is useful for pressing buttons (i.e., the buttons on a computer keyboard), and prosthetic attachment 33 is useful for grasping objects. Each prosthetic attachment 30-33 includes attachment piece 12.

Attachment Piece

FIG. 11 shows a top view of a preferred attachment piece 12. Magnet 13 is rigidly embedded into base 14 as shown, via a pressure fit. Contoured valleys 21A-21H and contoured peaks 20A-20H surround attachment piece 12 at its perimeter. As with base 14, attachment piece 12 is preferably plastic and preferably fabricated via an injection molded process.

As stated above in reference to FIGS. 6 and 7, as attachment piece 12 is moved closer to base 14 the magnetic attractive force between magnets 13 and 16 becomes sufficient to pull prosthetic attachment 11 close to prosthetic arm 1 so that attachment piece 12 and base 14 are rigidly connected (FIG. 7). Valleys 21 and 26 and peaks 25 and 20 function to guide prosthetic attachment 11 so that it is appropriately mated with prosthetic arm 1 as shown in FIG. 7.

It should be noted that the user is able to customize the desired angle of attachment of the prosthetic attachment. For example, aligning attachment piece 12 with base 14 such that peak 25A (FIG. 11) is mated with valley 21A (FIG. 16) produces prosthetic attachment 11 connected at specific connection angle (FIG. 17), with tip 11b faced downward. Alternatively, aligning attachment piece 12 with base 14 such that peak 25A is mated with valley 21B produces a prosthetic attachment connected at different connection angle (FIG. 18), with tip 11b facing outward from the page. Hence, the user is easily able to choose a connection angle to his liking.

Locking Device

Another preferred embodiment is shown in FIGS. 19A-20. Prosthetic attachment 11 utilizes a locking device to more securely attach attachment piece 12 to base 14. Locking sleeve 50 includes holes 62 and 63 drilled through the sleeve. Attachment piece 12 includes a plurality of holes 61 and base 14 includes a plurality of holes 60 (see FIG. 19A). After magnetic force has drawn together attachment piece 12 and base 14, both attachment piece 12 and 14 are locked together by the insertion of locking pins 64 through holes 62 and 63 of locking sleeve 50 and hole 61 of attachment piece 12 and hole 60 of attachment piece 14.

Another preferred embodiment is shown in FIGS. 21-22. Locking sleeve 80 is rigidly formed to the perimeter of attachment piece 12 and includes holes 63 drilled through the sleeve. Base 14 includes a plurality of holes 60. After magnetic force has drawn together attachment piece 12 and base 14, both attachment piece 12 and 14 are locked together by the insertion of locking pin 64 through hole 63 of locking sleeve 80 and hole 60 of base 14.

Another preferred embodiment is shown in FIGS. 23-24. Locking sleeve 90 is rigidly formed to the perimeter of base 14 and includes holes 63 drilled through the sleeve. Attachment piece 12 includes a plurality of holes 60. After magnetic force has drawn together attachment piece 12 and base 14, both attachment piece 12 and 14 are locked together by the insertion of locking pin 64 through hole 63 of locking sleeve 90 and hole 61 of attachment piece 12.

Other Preferred Embodiment

FIG. 24 shows another preferred embodiment of the present invention. In FIG. 24, base 14 is formed into prosthetic arm 1. Preferably base 14 is formed from plastic via an injection molding process. Attachment piece 12 and base 14 connect in a fashion similar to that described above in reference to earlier described embodiments.

Although the above-preferred embodiments have been described with specificity, persons skilled in this art will recognize that many changes to the specific embodiments disclosed above could be made without departing from the spirit of the invention. For example, although the above preferred embodiments discussed the utilization of magnets 13 and 16, it would be possible to substitute one of the magnets with a magnetic material. For example, either magnet 13 or magnet 16 could be substituted with a ferromagnetic material such as iron, cobalt, steel, nickel, or gadolinium. Also, although the above embodiments discuss the utilization of utilizing an injection molding process for manufacture, other methods are also possible, including 3D printing. Also, FIGS. 12-15 depicted multiple types of prosthetic attachments. It should be noted that this is only a small sampling and that many other types of prosthetic attachments are possible. Also although the above descriptions specifically discussed methods for attachment of a prosthetic attachment to a prosthetic arm, it should be noted that similar methods could be utilized to attach a prosthetic attachment to a other prosthetic limbs as well. For example, similar methods could be utilized to attach a prosthetic foot attachment to a prosthetic leg. Therefore, the attached claims and their legal equivalents should determine the scope of the invention.

What is claimed is:

1. A removably attachable prosthetic attachment for a prosthetic limb, comprising:
   A) a base rigidly attached to said prosthetic limb, said base comprising:
      1) a base magnet rigidly attached to said base,
      2) a plurality of base peaks and base valleys surrounding said base magnet, and
   B) an attachment piece rigidly attached to said prosthetic attachment, said attachment piece comprising:
      1) an attachment piece magnet rigidly attached to said attachment piece,
      2) a plurality of attachment piece peaks and piece valleys surrounding said attachment piece magnet,
      wherein a magnet force attracts said base magnet to said attachment piece magnet and
      wherein said base peaks and valleys mate with said attachment piece peaks and valleys for a secure removable attachment.

2. The prosthetic attachment as in claim 1 wherein said base is attached to said prosthetic limb via a bolt.

3. The prosthetic attachment as in claim 1, wherein said base is plastic and is formed into said prosthetic limb via an injection molding process.

4. The prosthetic attachment as in claim 1, wherein either said base magnet or said attachment piece magnet is a magnetic material.

5. The prosthetic attachment as in claim 1 further comprising a locking device.

6. The prosthetic attachment as in claim 5 wherein said locking device comprises a locking sleeve that is pin connected to said attachment piece and said base.

7. The prosthetic attachment as in claim 5 wherein said locking device comprises a locking sleeve formed to said attachment piece and pin connected to said base.

8. The prosthetic attachment as in claim 5 wherein said locking device comprises a locking sleeve formed to said base and pin connected to said attachment piece.

9. The prosthetic attachment as in claim 1, wherein said prosthetic attachment is a prosthetic hand and wherein said prosthetic limb is a prosthetic arm.

10. The prosthetic attachment as in claim 9 wherein the angle of attachment of said removable hand is adjustable.

\* \* \* \* \*